(12) United States Patent
Markus

(10) Patent No.: US 8,672,927 B2
(45) Date of Patent: Mar. 18, 2014

(54) LASER APPLICATOR

(75) Inventor: Kai Ulf Markus, Eschweiler (DE)

(73) Assignee: VIMECON GmbH, Herzogenrath (DE)

( * ) Notice: Subject to any disclaimer, the term of this patent is extended or adjusted under 35 U.S.C. 154(b) by 46 days.

(21) Appl. No.: 13/130,889

(22) PCT Filed: Nov. 25, 2009

(86) PCT No.: PCT/EP2009/065822
§ 371 (c)(1),
(2), (4) Date: May 24, 2011

(87) PCT Pub. No.: WO2010/060924
PCT Pub. Date: Jun. 3, 2010

(65) Prior Publication Data
US 2011/0230941 A1   Sep. 22, 2011

(30) Foreign Application Priority Data

Nov. 26, 2008 (DE) .......................... 10 2008 058 894

(51) Int. Cl.
*G02B 6/02* (2006.01)
*A61B 18/18* (2006.01)

(52) U.S. Cl.
USPC .................. 606/14; 606/13; 606/15; 606/16; 385/123

(58) Field of Classification Search
USPC ......... 606/2–19; 604/58, 96.01, 523; 385/123
See application file for complete search history.

(56) References Cited

U.S. PATENT DOCUMENTS

| | | | | |
|---|---|---|---|---|
| 5,248,311 A | * | 9/1993 | Black et al. | ...................... 606/15 |
| 5,722,426 A | | 3/1998 | Kolff | |
| 2007/0126950 A1 | | 6/2007 | Kurihara | |
| 2008/0117639 A1 | * | 5/2008 | Chen | ............................ 362/361 |
| 2008/0194973 A1 | | 8/2008 | Imam | |
| 2009/0274426 A1 | * | 11/2009 | Lail | ............................. 385/105 |
| 2009/0275931 A1 | | 11/2009 | Markus | |

FOREIGN PATENT DOCUMENTS

| | | |
|---|---|---|
| DE | 102006039471 B3 | 3/2008 |
| JP | 58001103 A | 6/1983 |
| WO | 2007118745 A1 | 10/2007 |

\* cited by examiner

*Primary Examiner* — Ahmed Farah
*Assistant Examiner* — William Cheng
(74) *Attorney, Agent, or Firm* — Fay Sharpe LLP

(57) ABSTRACT

A laser applicator includes an optical fiber with a core surrounded by a cladding. The cladding contains openings (40) for coupling radiative energy outward. To accomplish an even distribution of energy, the size of the opening increases from the proximal end to the distal end. The openings (40) are combined into groups (45), with the number of openings within a group varying. The openings (40) are of a uniform size so that the area of decoupling (13) can be produced in a simple manner.

11 Claims, 2 Drawing Sheets

LASER APPLICATOR

BACKGROUND

The invention refers to a laser applicator with an elongate catheter comprising an inner core and a cladding surrounding the core, wherein the cladding comprises a series of openings in a decoupling portion, whose opening surface increases towards the distal end.

Such a laser applicator is described in US 2009/0275931 (Vimecon), the disclosure of which is incorporated into the present application by reference. The known laser applicator comprises an elongate flexible catheter including a light guide. The distal end section is formed into a lariat-like shape whose plane extends transversely to the main portion of the catheter. Laser radiation is input into the light guide at the proximal end. A decoupling portion exists at the distal end of the catheter, where the energy is coupled laterally out of the light guide and exits from the catheter.

In particular, the laser applicator serves for the treatment of atrial fibrillation and other types of cardiac arrhythmia. It can be used to cauterize cardiac tissue by converting light energy into thermal energy. The laser radiation exiting the light guide heats the surrounding tissue to values above 60° C., resulting in the denaturation of proteins and the formation of an electrically inactive scar. For the purpose of achieving a uniform distribution of the decoupled energy over the length of the decoupling path, the width of the circular cladding segment that causes the decoupling can be varied over the decoupling path.

DE 10 2006 039 471 B3 describes a laser applicator comprising a catheter with a light guide. In a distal end section of the catheter, the cladding of the light guide has a cutout from which light exits laterally from the light guide. While the intact cladding of the light guide effects total internal reflection so that the light energy is transported in the longitudinal direction of the light guide, the cutouts at the border of the light guide core cause refraction so that light energy is coupled out. The cutouts are discrete openings of round cross section. Their diameter increases constantly from one opening to the next in the direction of the distal end of the light guide and varies from a size of 20 μm for the first opening to a size of 100 μm for the last opening. In a certain variant, the distances between two respective neighboring openings decrease in the direction of the distal end of the light guide fiber. This is to compensate for the decrease in radiance in the light guide fiber in the direction of its distal end.

Providing the openings for the lateral decoupling of laser energy from the light guide requires high precision, wherein the enlargement of the exit surface must be made in very small increments from the distal end to the proximal end.

The present application addresses the problem of making a decoupling path in a light guide by opening the cladding of the light guide in order to achieve an energy density of the decoupled radiation that is uniform over the length of the decoupling portion.

SUMMARY

An object is to provide a laser applicator whose decoupling cross section, increasing from the proximal to the distal end, can be realized in a relatively simple manner and with high precision.

In accordance with one aspect, a laser applicator has openings that are of uniform size and that are combined into spaced groups, wherein the number of openings increases from one group to the next towards the distal end.

These openings are made uniformly. Generally, these are openings of equal diameter. Such openings can be burned into the cladding of the light guide using a laser. The openings of uniform size are formed as a linear structure, i.e. a single-row chain of openings. The uniform openings can be readily formed using a laser beam. The openings are combined into groups, wherein the overall cross section of the openings increases from one group to the next in the distal direction.

Although the openings are formed with a uniform size, the invention does not exclude that different types of openings are realized in individual portions of the row of openings. In any case, however, the openings of one group have the same diameter. Preferably, all openings of the decoupling portion have the same diameter.

The groups of openings may be spaced from each other without the efficiency of a thermal tissue treatment along a continuous line being substantially affected thereby. The thermal treatment tolerates short interruptions of the welding line. This is used to divide the row of openings into groups of openings having mutual distances of less than 500 μm. Preferably, the distances between the groups are substantially equal.

The openings within a group are arranged along a line. Preferably, the openings of all groups are arranged along a straight line.

The openings of a group should be arranged rather close to each other. Preferably, their mutual distance is smaller than the diameter of an opening.

For the purpose of a fine grading of the hole surface increasing in the proximal direction of the decoupling section, it may be provided that at least two openings of a group partly overlap each other, whereby a blended hole is formed. The degree of overlap can become smaller from one group to the next in the direction of the distal end so that the surface of the blended holes becomes larger in the distal direction. This allows for a quasi-continuous increase in the cross-sectional area, the increment being independent of the size of the holes. The blended hole is preferably provided at the distal end of the group.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

In the Figures.

DETAILED DESCRIPTION

Figure 1:
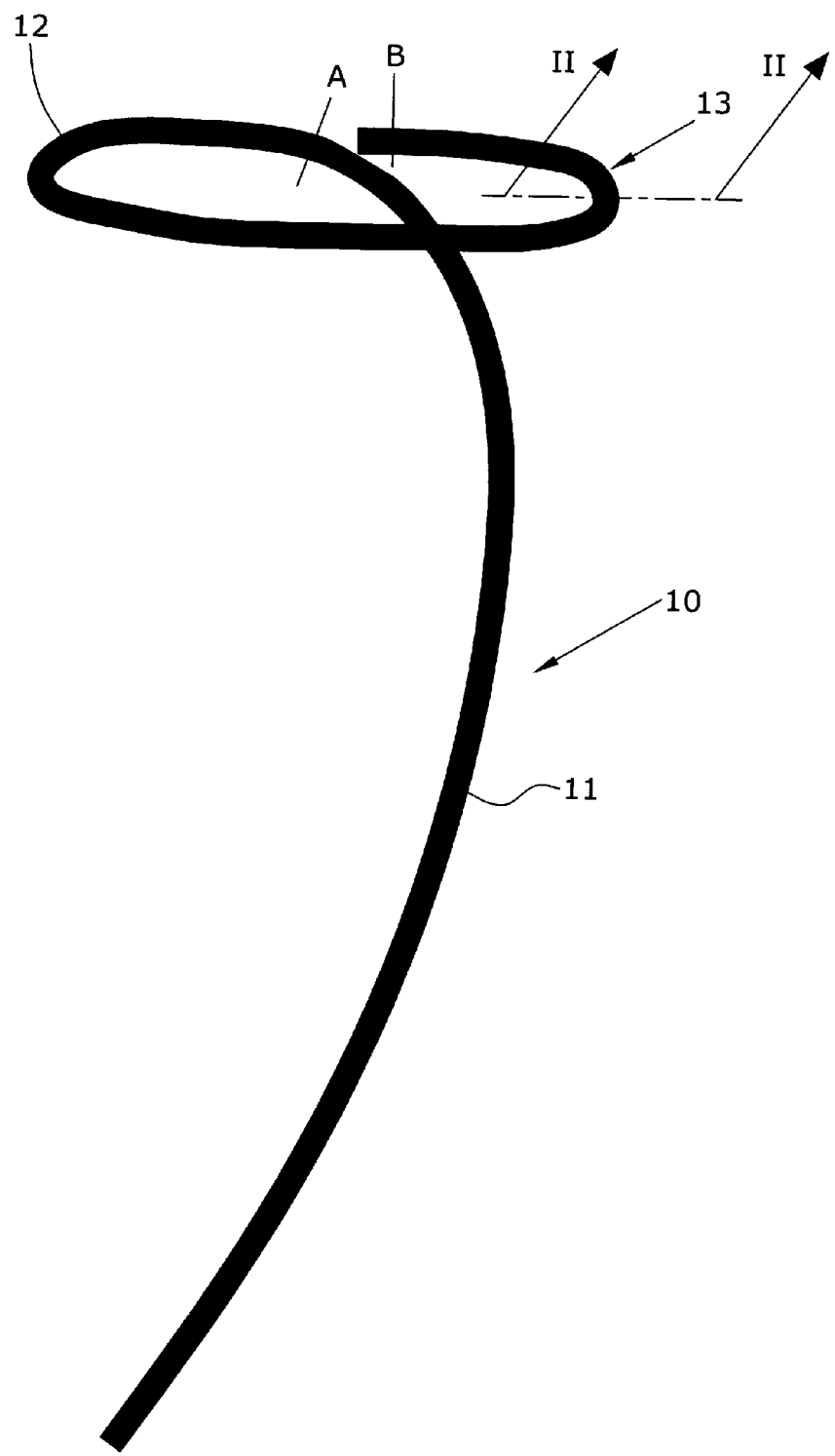
FIG. 1 is a schematic illustration of the general structure of the laser applicator.

The laser applicator comprises a catheter 10 in the form of an elongate strand. The catheter has one or a plurality of lumens. It is preformed in the manner illustrated in FIG. 1 and is composed of a proximal section 11 and a distal end section 12. Whereas the proximal section 11 extends substantially linearly, the distal end section 12 is formed into a loop shaped as a circle open at one point. The plane of the loop is transverse, in particular at a right angle, with respect to the longitudinal direction of the proximal section. It is dimensioned such that it contacts the wall of a blood vessel from inside with slight pressure. The outer diameter of the loop is about 4-6 mm.

The position A indicates the transition from the proximal section 11 to the end section 12. The position B indicates the distal end of the distal end section. The decoupling portion 13, where laser energy is coupled laterally out from the catheter, extends from the position A to the position B.

Figure 2:
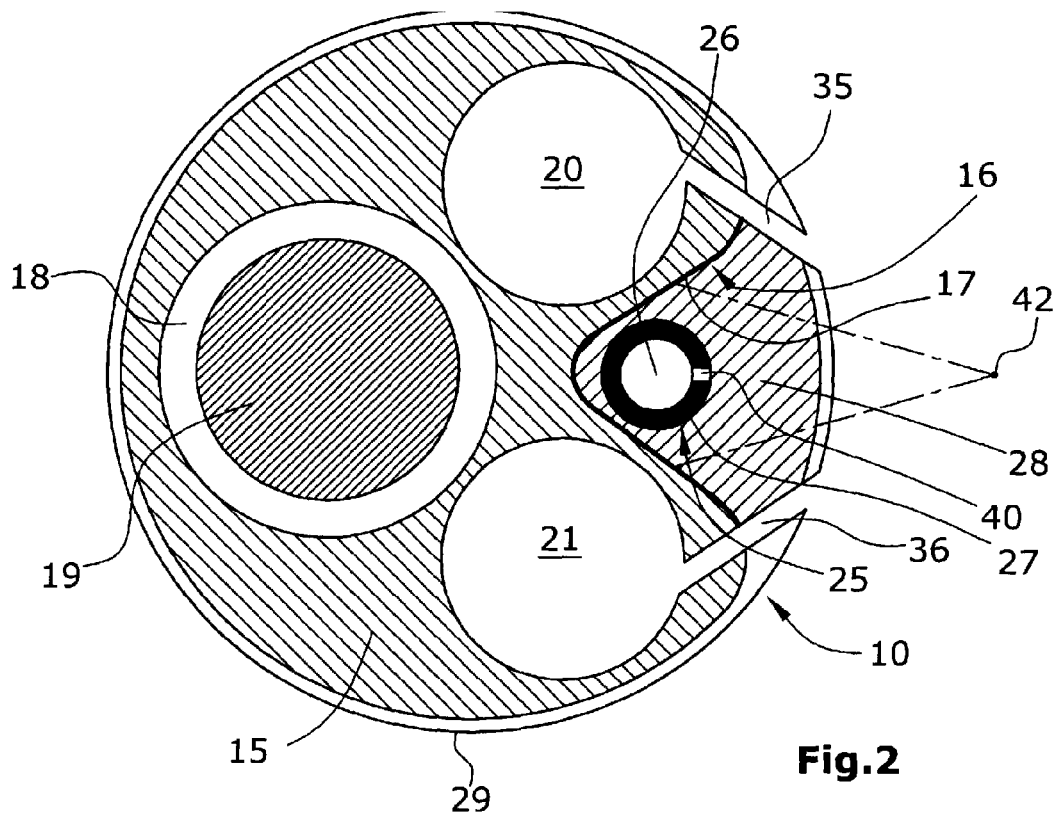
FIG. 2 is a cross section along line II-II in FIG. 1.

In the decoupling portion 13, the laser applicator has the cross section illustrated in FIG. 2. It has an integral elongate catheter body 15 of generally circular cross section and provided with a generally V-shaped groove. The groove 16 has two outwardly diverging flanks covered with a reflective layer 17. The groove 16 extends up to near the longitudinal center axis of the catheter body 15.

The catheter body 15 includes a lumen 18 for a form wire 19, as well as two longitudinal cooling channels 20 and 21 extending along the entire length of the catheter.

A light guide 25 is set into the groove 16 from outside. The same has a core 26 and a cladding 27 surrounding the core, the material of the cladding having a lower refraction index than the core. The light guide 25 is fastened in the groove 16 by means of a transparent adhesive 28. On the outer side, the catheter is sheathed by a transparent covering hose 29.

In the decoupling portion, the cooling channels 20, 21 are provided with outlet bores 35, 36 that converge towards each other and eject cooling jets outward. The outlet bores extend under an acute angle with respect to each other. They make the cooling jets impinge on the target area of the heat radiation. The outlet bores have corresponding openings in the covering hose.

The light guide 25 is first machined outside the catheter by making openings 40 in the form of small bores in the decoupling portion 13. The holes are burnt thermally into the material of the cladding by means of a focused laser beam. The light guide thus prepared is set into the lateral groove 16 of the catheter body 15 and is then fixed by means of the adhesive 28. Thereafter, the covering hose 29 is applied.

The openings 40 in the cladding of the light guide are directed radially outward with respect to the center axis of the catheter body 15. The adhesive 28 includes dispersing particles. The radiation escaping from the core 26 of the light guide is scattered at the particles and is reflected by the reflective layer 17 so that the radiation is focused at the focal point 42 where it acts on the body tissue.

Figure 3:
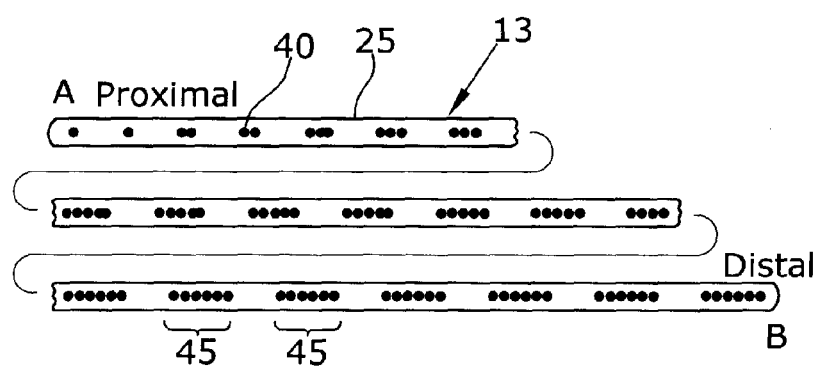
FIG. 3 is a schematic illustration of the groups of openings in the cladding of the light guide from the proximal end to the distal end of the decoupling portion.

FIG. 3 illustrates the arrangement of the openings 40 in the longitudinal direction of the light guide 25 along the length of the decoupling portion. The position A indicates the proximal end and the position B indicates the distal end of the decoupling portion 13. In order to achieve a distribution of the laterally escaping energy that is as uniform as possible, the decoupling cross section has to increase towards the distal end.

The openings 40 in the cladding 27 of the light guide 25 are bores of a diameter of 75 µm, thermally formed by means of a corresponding laser beam. The openings 40 are uniform in size. They all have the same diameter. All openings 40 are arranged in a linear array. They are combined into groups 45. The number of openings in a group 45 varies. It increases from the proximal end A to the distal end B. It is obvious that the first group is formed by only one opening. Thereafter, the groups become ever larger, i.e. they include more openings. The openings in a group are generally equidistant. They are arranged such that they just do not blend. The groups 45 are spaced apart. Here, the distance is 400 µm. Thus, the distance between the groups is constant along the decoupling portion.

Figure 4:
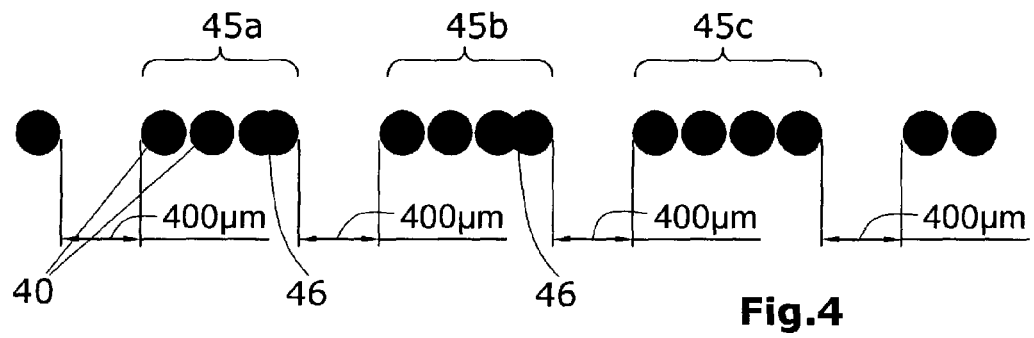
FIG. 4 is an enlarged illustration of neighboring groups of openings.

FIG. 4 is an enlarged illustration of a series of groups 45a, 45b, 45c. Here, the last openings of the group are combined into a blended hole 46. The blended hole is formed by the overlapping of two holes, with the degree of overlap differing for the groups 45a and 45b. Here as well, the distance between the groups is 400 µm. By blending two openings, the overall cross section of a group can be varied with a fine grading. Thus, the overall cross section is increased quasi continuously from group 45a via group 45b to group 45c. The blended hole 46 is situated at the distal end of a respective group.

The invention allows making the openings as uniform openings, where the only varying parameter for a change in the outlet cross section is the linear position of the openings.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A laser applicator with an elongate light guide comprising:
an inner core and a cladding surrounding the core, wherein the cladding has a series of openings in a decoupling portion, the openings being uniform in size and combined into mutually axially spaced groups, each group having a plural number of openings, the number of openings increasing from one group to the next towards a distal end.

2. The laser applicator of claim 1, wherein the openings in a group are arranged along a straight line.

3. The laser applicator of claim 1, wherein the openings of a group are spaced from each other by a distance smaller than the diameter of an opening.

4. The laser applicator of claim 1, wherein at least two openings of a group overlap in part, such that a blended hole is formed.

5. The laser applicator of claim 4, wherein a degree of overlap decreases from one group to the next towards the distal end so that the area of the blended holes increases in the distal direction.

6. The laser applicator of claim 4, wherein the blended hole is arranged at the distal end of a respective group.

7. The laser applicator of claim 1, wherein the cladding is configured to reflect emitted light in the core back into the core.

8. A laser applicator comprising:
an elongated light guide including an inner core and a reflective cladding surrounding the core;
a series of openings of uniform size defined in the cladding to allow light to escape from the light guide therethrough, the openings being divided into a series of axially spaced groups of openings, each group having a plurality of openings, a total area of the openings in each group increasing progressively towards a distal end from a proximal end.

9. The laser applicator of claim 8, wherein in each group, some of the openings are connected.

10. The laser applicator of claim 8, wherein at least a distal end pair of openings of each group overlap each other.

11. The laser applicator of claim 8, wherein the openings of each group are disposed in a straight line.

* * * * *